(12) United States Patent
Lee et al.

(10) Patent No.: US 7,252,962 B2
(45) Date of Patent: Aug. 7, 2007

(54) METHOD FOR DETECTING SENSITIVITY TO ACETYLCHOLINE ESTERASE IN INSECTS

(75) Inventors: Han Lim Lee, Selangor (MY); Wasi Ahmad Nazni, Selangor (MY)

(73) Assignee: Institute for Medical Research, Wilayah Persekutuan (MY)

( * ) Notice: Subject to any disclaimer, the term of this patent is extended or adjusted under 35 U.S.C. 154(b) by 446 days.

(21) Appl. No.: 10/320,710

(22) Filed: Dec. 17, 2002

(65) Prior Publication Data

US 2004/0101923 A1     May 27, 2004

(30) Foreign Application Priority Data

Nov. 26, 2002   (MY) ............................. PI 2002 4415

(51) Int. Cl.
    *C12Q 1/46*        (2006.01)
(52) U.S. Cl. ......................................... 435/20; 435/183
(58) Field of Classification Search ................... 435/19, 435/4, 975, 20, 29, 69.2, 183
    See application file for complete search history.

(56) References Cited

U.S. PATENT DOCUMENTS 5,686,237 A * 11/1997 Al-Bayati ...................... 435/4

OTHER PUBLICATIONS

CDC, "Evaluating Mosquitoes for Insecticide Resistance"(Web-Based Instruction), www.cdc.gov/ncidod/wbt/resistance/assay/microplate/step_2.htm, (May 2002).*

Arufe M. Oxidation of Cholinesterase Inhibiting Pesticides. Biochemical Education 28(3)174-177, 2000.*

* cited by examiner

*Primary Examiner*—Ralph Gitomer
(74) *Attorney, Agent, or Firm*—Lowe Hauptman & Berner LLP

(57) ABSTRACT

A method for checking for sensitivity of acetylcholine esterase in insects using a single insect, includes homogenizing a single insect in aqueous, neutral to acid pH phosphate buffer, providing a solution of acetylcholine iodide in neutral to acid pH phosphate buffered water-miscible organic solvent, providing a solution of 5,5-dithio-bis-(2-nitrobenzoic acid) in the buffer, and providing a solution of propoxur in the buffer, dropping the insect homogenisate into the wells of an assay plate, dropping the acetylcholine iodide and 5,5-dithio-bis-(2-nitrobenzoic acid) solutions into some of the wells and 5,5-dithio-bis-(2-nitrobenzoic acid) propoxur solutions into the other wells and checking for a difference in the yellow coloration between the samples in the two sets of cells.

11 Claims, No Drawings

METHOD FOR DETECTING SENSITIVITY TO ACETYLCHOLINE ESTERASE IN INSECTS

This invention relates to a method and test kit for determining insect resistance to insecticides and more particularly provides a method and test lit for determining insect resistance to organophosphate and carbamate based insecticides.

BACKGROUND TO THE INVENTION

Chemical insecticides remain as the most important agents for the control of vector-borne diseases such as malaria, dengue, filartasis etc. Countless deaths from these diseases have been spared since the introduction of the first synthetic insecticide, DDT in the 1940's. Prolonged use of insecticides has however, induced the development of resistance in the vectors, primarily insects, that carry such diseases, which renders them less effective in combating the vectors and thus the diseases that they spread. Resistance detection is mainly based on the World Health Organization (WHO) standard test procedures which, among other things, are not user-friendly, are time-consuming; require many insect specimens, use test kits of short shelf life and need skilled manpower to conduct the tests and interpret the test results. As a result, very often little is known of the susceptibility status of many insect vectors, which tends to affect the outcomes of control programmes.

The development of rapid field test kits would be a major breakthrough in the control of vector-borne diseases.

In general, the biochemical basis of resistance is due to one of three mechanisms:
1) increased level of non-specific esterases targeted against organophosphates and carbamates;
2) elevated activity of mixed-function oxidases against pyretroids; and
3) non-susceptibility of acetylcholine esterase against organophosphates and carbamates.

SUMMARY OF THE INVENTION

This invention provides a method and test kit for determining susceptibility of acetylcholine esterase in insects using a single insect, that is quick and easy to use and produces results that are very simple to interpret.

According to the invention the test kit comprises a container containing separate containers of:
I. a neutral to acid pH phosphate buffer solution
II. acetylcholine iodide
III. 5,5-dithio-bis-(2-nitrobenzoic acid)
IV. propoxur (a carbamate based insecticide) and
V. a water-miscible organic solvent.

For field use the kit will also contain the equipment for carrying out the test, for example mixing containers, test tubes, for example Eppendof tubes, pipettes and a microassay plate.

The buffered pH is preferably between 6 and 7, more preferably about 6.8.

The pH buffer is preferably potassium phosphate.

The propoxur is preferably used as solution of 5 to 25 mg/l in 70% ethanol.

The water-miscible organic solvent is preferably acetone.

The method of the invention comprises the steps, in any order, of homogenizing a single insect in the buffer, preferably by grinding it in a small tube, such as an Eppendorf tube, with a pestle, producing a solution of acetylcholine iodide in buffered solvent, producing a solution of 5,5-dithio-bis-(2-nitrobenzoic acid) in the buffer, and producing a solution of propoxur in the buffer, and then dropping the insect homogenisate into the wells of an assay plate, dropping the acetylcholine iodide and 5,5-dithio-bis-(2-nitrobenzoic acid) solutions into some of the wells and 5,5-dithio-bis-(2-nitrobenzoic acid), acetylcholine iodide and propoxur solutions into the other wells and checking for a difference in the yellow coloration between the samples in the two sets of cells.

If desired, the propoxur and acetylcholine iodide solutions may be pre-mixed.

The results may be determined by eye or, if more accurate results are needed, by scanning using an immunoassay reader at 410 nm.

If the yellow coloration in the cells containing propoxur becomes lighter after an incubation period the enzyme acetylcholine esterase is susceptible and the insect is not resistant to organophosphate and carbamate based insecticides.

The invention has the advantage of being the first available field test kit for testing for acetylcholine esterase susceptibility that requires only a single insect for testing and that can be used in a test that gives rapid test results (they are usually obtainable within 30 minutes) that can be read visually and colorimetrically without equipment. The test kits and method also require less skilled manpower and are easy to use without special training. Moreover, the kits have a long shelf life and are stable for weeks at room temperature.

Use of the kit will
1. considerably simplify resistance detection
2. ensure that chemical insecticides used to control pests and disease vectors are effective and hence save lives, cost and manpower
3. allow constant and regular monitoring of the susceptibility of target insects and
4. assist in the design of new control agents, countermeasures and understanding of the mode of action of insecticides.

DESCRIPTION OF PREFERRED EMBODIMENT

Eight containers were prepared containing, respectively 10 ml of potassium phosphate buffer (pH 6.8)×2, 1 ml of acetone, 7.5 mg acetylcholine iodide, 9 ml of potassium phosphate buffer, 1.3 mg of 5,5-dithio-bis-(2-nitrobenzoic acid), 1 mg propoxur as a solution of 25 µg in 10 ml 70% ethanol and ml of potassium phosphate buffer.

The acetone is poured into the acetylcholine iodide and mixed well to form a solution, which is then added to the 9 ml buffer. One of the 10 ml buffers is poured into the 5,5-dithio-bis-(2-nitrobenzoic acid) and mixed well to form a solution, 1.8 ml of the acetylcholine iodide solution is mixed with the 4 ml buffer and 0.2 ml is then added and mixed well.

A single mosquito is homogenized in one drop of the buffer in an Eppendorf tube using a pestle and further diluted with buffer to the 0.5 ml mark on the Eppendorf tube. After the homogenisate has stood for 5 minutes to allow debris to settle one drop of the homogenisate is dropped into each well of a four well micro-assay plate. One drop of the undiluted acetylcholine iodide solution and one drop of the 5,5-dithio-bis-(2-nitrobenzoic acid) solution are dropped into two of the wells. One drop of the propoxur solution is dropped into the other two wells. One drop of the 5,5-dithio-bis-(2-nitrobenzoic acid) solution is then-dropped into these two wells. The plate was incubated for 30 minutes and then the colour in the samples in the two sets of wells was assessed. If the yellow colour in the second pair of wells containing propoxur solution is lighter than that in the first pair of wells the mosquito is susceptible to acetylcholine esterase and therefore not resistant to organophosphate and carbamate based insecticides.

Colour can be checked by eye or by scanning using an immunoassay reader at 410 nm.

The invention claimed is:

1. A method for detecting acetylcholine esterase sensitivity to insecticides in insects, comprising:
   homogenizing a single insect in a neutral to acid pH phosphate buffer and forming an insect homogenisate,
   providing a solution of acetylcholine iodide in a neutral to acid pH phosphate-buffered water-miscible organic solvent,
   providing a solution of 5,5-dithio-bis-(2-nitrobenzoic acid) in the phosphate buffer,
   providing a solution of propoxur in the phosphate buffer,
   introducing the insect homogenisate into at least one first well and at least one second well of an assay plate, then introducing the acetylcholine iodide and 5,5-dithio-bis-(2-nitrobenzoic acid) solutions into the at least one first well and 5,5-dithio-bis-(2-nitrobenzoic acid), acetylcholine iodide and propoxur solutions into the at least one second well,
   detecting a difference in yellow coloration between samples in the first and second cells, and
   correlating the yellow coloration difference observed in the first and second cells with acetylcholine esterase sensitivity to insecticide in the single insect.

2. The method of claim 1, wherein the buffer is a pH 6 to 7 buffer.

3. The method of claim 2, wherein the buffer is a pH 6.8 buffer.

4. The method of claim 2, wherein the buffer contains potassium phosphate.

5. The method of claim 1, wherein the propoxur comprises a solution of 5 to 25 mg/l propoxur in ethanol.

6. The method of claim 1, wherein the propoxur and acetylcholine iodide solutions are pre-mixed.

7. The method of claim 1, wherein said water-miscible organic solvent is acetone.

8. The method of claim 1, wherein the color difference detection is carried out visually.

9. The method of claim 1, wherein the color difference detection is carried out using an immunoassay reader at 410 nm.

10. The method of claim 1, wherein the insect is a mosquito.

11. The method of claim 1, which determines susceptibility of acetylcholine esterase in insects to organophosphate—or carbamate-based insecticides.

* * * * *